(12) United States Patent
Shoham et al.

(10) Patent No.: US 7,887,567 B2
(45) Date of Patent: Feb. 15, 2011

(54) APPARATUS FOR SPINAL FIXATION OF VERTEBRAE

(75) Inventors: Moshe Shoham, M.P. Hamovil (IL); Boris Silberstein, Haifa (IL); Michael Burman, Haifa (IL)

(73) Assignee: Mazer Surgical Technologies, Ltd., Caesarea (IL)

( * ) Notice: Subject to any disclaimer, the term of this patent is extended or adjusted under 35 U.S.C. 154(b) by 1220 days.

(21) Appl. No.: 10/595,305

(22) PCT Filed: Oct. 5, 2004

(86) PCT No.: PCT/IL2004/000919

§ 371 (c)(1),
(2), (4) Date: Jun. 14, 2006

(87) PCT Pub. No.: WO2005/032325

PCT Pub. Date: Apr. 14, 2005

(65) Prior Publication Data

US 2008/0071272 A1    Mar. 20, 2008

Related U.S. Application Data

(60) Provisional application No. 60/508,288, filed on Oct. 6, 2003.

(51) Int. Cl.
*A61B 17/56* (2006.01)
*A61B 19/00* (2006.01)

(52) U.S. Cl. .................................. 606/279; 606/86 R (58) Field of Classification Search .................. 606/64, 606/151, 102, 54, 56, 60, 87, 90, 97, 130, 606/59, 246, 250, 253, 256, 257, 260, 261, 606/264, 278, 279, 300, 301, 329; 600/426, 600/429; 403/66, 85, 100, 180; 128/103.1
See application file for complete search history.

(56) References Cited

U.S. PATENT DOCUMENTS 3,242,922 A    3/1966    Thomas (Continued)

FOREIGN PATENT DOCUMENTS

JP    09-285473    11/1997

(Continued)

OTHER PUBLICATIONS

International Search Report and Written Opinion of International Application No. PCT/IL04/00919 mailed Dec. 19, 2005.

*Primary Examiner*—Eduardo C Robert
*Assistant Examiner*—David Comstock
(74) *Attorney, Agent, or Firm*—Fish & Richardson P.C.

(57) ABSTRACT

A framed device in the form of a bridge for fixing a number of vertebrae together into positions which are uniquely defined relative to the bridge, but which can move with the spine relative to the external environment. The fixation generated by such a bridge is especially useful in Computer Assisted Surgery procedures, either using manual navigation and a tracking system to follow the position of the surgeon's tools relative to the operated vertebrae, or by using a pre-programmed robot mounted on the bridge itself to perform the surgery. Alternative embodiments of the bridge may be used either for performing surgery in one procedure on a number of vertebrae of the spine, or as a reference frame for performing surgery at different locations along the spine, while providing an alignment reference along major lengths or along all of the spine.

8 Claims, 5 Drawing Sheets

U.S. PATENT DOCUMENTS

| | | | | |
|---|---|---|---|---|
| 4,361,144 A * | 11/1982 | Slatis et al. | | 606/54 |
| 4,448,191 A | 5/1984 | Rodnyansky et al. | | |
| 4,919,119 A * | 4/1990 | Jonsson et al. | | 606/54 |
| 5,403,314 A | 4/1995 | Currier | | |
| 5,443,464 A * | 8/1995 | Russell et al. | | 606/54 |
| 5,531,747 A | 7/1996 | Ray | | |
| 5,645,548 A * | 7/1997 | Augsburger | | 606/87 |
| 5,674,221 A | 10/1997 | Hein et al. | | |
| 5,810,814 A * | 9/1998 | Newson | | 606/59 |
| 5,891,157 A * | 4/1999 | Day et al. | | 606/130 |
| 6,162,223 A * | 12/2000 | Orsak et al. | | 606/59 |
| 6,226,548 B1 * | 5/2001 | Foley et al. | | 600/426 |
| 6,322,567 B1 | 11/2001 | Mittelstadt et al. | | |
| 6,428,540 B1 * | 8/2002 | Claes et al. | | 606/53 |

FOREIGN PATENT DOCUMENTS

| | | |
|---|---|---|
| JP | 2000-350731 | 12/2000 |
| WO | WO 8803395 A1 * | 5/1988 |
| WO | WO03/009768 | 2/2003 |

\* cited by examiner

APPARATUS FOR SPINAL FIXATION OF VERTEBRAE

CROSS REFERENCE TO PRIOR APPLICATION

The above-referenced application is the U.S. National Phase of International Patent Application PCT/IL2004/00919, filed Oct. 5, 2004, which claims priority from U.S. Provisional Application No. 60/508,288, which is incorporated by reference herein. The International application was published in English on Apr. 14, 2005 as WO 2005/032325 A2.

FIELD OF THE INVENTION

The present invention relates to the field of devices and methods for facilitating the performance of surgery on a number of vertebrae in a single procedure, and especially using robotic execution of the procedure, computer assisted techniques, or frame-aligned manual surgery.

BACKGROUND OF THE INVENTION

In a conventional surgical operation, the surgeon operates on an organ using his visual and tactile senses in order to locate his hand and the surgical tool in the correct position. In Computer Assisted Surgery (CAS) however, the motion of the surgical tool is generally determined by a pre-operative plan, with the actual operating location being pre-planned using pre-operative X-ray, CT, MRI or other images. During the operation, it is necessary to transfer this planning information to the operation site, generally by mutually referencing the coordinate system of the patient, the position of the surgical tool and the data provided by the pre-operative plan. This is known as a registration procedure.

It is therefore important to provide the computer with accurate information concerning the patient position relative to the navigation/robotic system. This is accomplished in contemporary CAS devices by either holding the body part on which the operation is being performed, in a fixed position following the registration process, or by attaching a dynamic referencing device which moves with the body part being operated on, and compensates for undesired motion by means of dedicated tracking software.

In spinal operation CAS procedures, if the procedure is to be performed on more than one vertebra, it is necessary, according to prior art methods, to affix dynamic referencing sensors at each level of the spine, or even on each vertebra, so that relative motion between different regions of the spine or even between different vertebrae can be detected and compensated for. Alternatively, all of the vertebra to be operated on are fixed to a stationary frame to ensure well-defined positions. Both of these alternatives are complex and inconvenient procedures.

There therefore exists an important need to provide a method of enabling CAS to be performed on several vertebrae in a single procedure, by means of a simple apparatus.

Additionally, when surgery is to be performed to correct or treat conditions related to spinal curvature, according to prior art methods the surgeon has generally used visual means for estimating the position of the vertebrae at different levels of the back. Such visual estimation, whether based on manual manipulation of the operating tools, or CAS guidance thereof, is potentially inaccurate and highly dependent on the surgeon's skill. There therefore also exists a need to provide a reference method for providing the surgeon with information about the relative location of vertebrae over the whole length of the spine.

SUMMARY OF THE INVENTION

There is thus provided, according to various preferred embodiments of the present invention, novel frame devices for use in fixing a number of vertebrae together into positions which are uniquely defined relative to the frame. Such fixation is especially useful in two applications of spinal surgery:

(i) as a reference frame for Computer Assisted Surgery procedures performed on a number of vertebrae of the spine in one procedure, either using manual navigation and a tracking system to follow the position of the surgeon's tools relative to the operated vertebrae, or by using a pre-programmed robot to perform the surgery; and (ii) as a reference frame for use in performing surgical procedures at locations along the entire length of the spine of a subject, or a major part thereof, when it is necessary to provide a reference for the alignment of major lengths of the spine or of all of the spine.

According to a first preferred embodiment of the present invention, there is provided a reference bridge that fixes several vertebra together to generate a single frame of reference for all of those vertebrae. This bridge differs from prior art vertebrae fixing devices in that although it is fixed above the spine and is fixed relative to the vertebrae, it is allowed to move in space as a single unit with movement of the spine relative to the operating table. A dynamic referencing sensor, a miniature robot or a passive measuring arm operating as a mechanical digitizer, can be attached to this reference bridge, and since each of the relevant vertebrae are affixed to the bridge, a single registration procedure can be used to define the relative position and orientation of each of the vertebra and of the frame itself, relative to the operation planning environment, whether a preoperative CT or MRI image, or an intra-operative X-ray fluoroscopic image, or any other. This thus obviates the prior art need either for individual registration of each vertebra, or for fixing of all of the vertebrae relative to the operating table.

The reference bridge is generally fixed only to a limited number of vertebrae, such that only those vertebrae fixed by some means to the bridge can be considered as having a positively defined position relative to the bridge. However, since the relative allowed motion between neighboring vertebrae is small, even unattached vertebrae next to, or close to, vertebrae attached to the bridge, can also be considered to have reasonably well defined positions relative to the bridge. The required precision of the surgical procedure to be performed determines to what extent the positions of such unattached "neighboring vertebrae" can be assumed to be sufficiently precisely known.

It is to be understood that terms such as "above the spine" or "above a vertebra", or similar, as used in this application, and as claimed, are not meant to define a position in absolute space, but rather to indicate a general disposition relative to the spine or vertebrae. Since the usual position for performing spinal surgical procedures is when the subject is supine, the term "above" is used to describe this general disposition, though is not meant to limit the invention to the use of mutually vertical relative positions.

Once their relative position is known, the vertebrae can then be accurately operated upon, either using a navigation system or a bone mounted or bridge mounted robot. The preferred use of a bone mounted or bridge mounted robot is an advantageous embodiment, because it obviates the need to know where the vertebrae are relative to the environment, being concerned only with the relative position of the vertebrae to each other and to the bridge, since the robot position is known relative to either of them.

According to another preferred embodiment of the present invention, the bridge is used with a navigation system external to the bridge, in which the bridge ensures that the referencing to each vertebrae is known, not only relative to each other vertebra, but also absolutely in space, and hence relative to the external navigation system. In such embodiment, a tracking system is used to ensure correct positioning of the surgeon's tools relative to the bridge and hence to each vertebra.

When utilized for executing the first group (i) of applications mentioned hereinabove, the bridge according to these preferred embodiments of the present invention, is operative in the fixation of the positions of several, generally adjacent or closely spaced vertebra to the bridge. When utilized for executing the second group (ii) of applications mentioned hereinabove, the bridge preferably takes the form of a long frame extending in its maximum configuration, from the pelvis to the skull, preferably with fixation at the skull and the pelvis, and at selected vertebral points between them. According to further preferred embodiments of the present invention, the long frame bridge can extend, if not over the whole length of the spine, then at least over large parts thereof, such as from the skull to the bottom of the thoracic level, or from the pelvis to the bottom of the cervical level. In any of the long frame embodiments, the bridge is preferably divided into several parts, preferably at least one central section generally covering the thoracic section of the spine, a lower section covering the lumbar region, and an upper section covering the cervical section. In those embodiments where the bridge is fixed relative to the skull, There are several indications in which the present invention can be advantageously applied, the indications being listed according to the spinal region of their application:

A. Surgical Indications for the Cervical Region
  1. Atlantoaxial Instability, (C1-C2 Injuries)-Magerl technique of transarticular C1-C2 screw fixation.
  2. Radiculopathy, when present, due to entrapment of an exiting nerve root within a collapsed neuroforamen.
  3. Syndrom a vertebralis due to segmental cervical spine instability.
  4. Fractures of vertebral bodies.
  5. Spinal vertebral body tumor with adjacent vertebral body fusion.
  6. Failed decompressive operations with syndrome of cervical spine instability (status post laminectomy).

B. Surgical Indications for the Thoracic and Lumbar Regions
  1. Mechanical back pain.
  2. Radiculopathy, when present, is due to entrapment of an exiting nerve root within a collapsed neuroforamen.
  3. Spondylolisthesis.
  4. Fractures of vertebral bodies
  5. Spinal vertebral body tumor with adjacent vertebral body fusion.
  6. Failed previous fusion (pseudoarthrosis).
  7. Failed decompressive operations with syndrome of lumbar spine instability.
  8. Scoliosis correction.

There is therefore provided in accordance with a preferred embodiment of the present invention, a bridge for use in surgery on the vertebrae of the spine of a subject, the bridge comprising (i) a first support member for attaching at one end to a first vertebra in the spine of the subject, (ii) at least a second support member for attaching at one end to a second bone of the subject, and (iii) a cross member attached to the first and second support members at positions remote from the ends of the support members attached to the subject, such that the cross member is positioned proximate the spine of the subject. The second bone of the subject may preferably be a second vertebra of the subject's spine, the subject's skull, or the subject's pelvic bone. In any of the above mentioned embodiments of the present invention, the bridge is preferably such that it is free to move with movement of the spine of the subject. Furthermore, in any of the above-mentioned bridge embodiments, the first support member may preferably be attached to the first vertebra in the spine of the subject by means of a bone clamp, or it may be a K-wire.

According to a further preferred embodiment, the bridge may also comprise at least one additional support element for attaching the cross member to at least one additional vertebra of the spine, such that the first vertebra, the second bone and the at least one additional vertebrae have fixed positions relative to the bridge. The at least one additional support element may preferably be a K-wire.

In accordance with still another preferred embodiment of the present invention, in the above-described bridge, the cross member may preferably be adapted to accommodate a surgical robot, such that the robot can perform surgical procedures on at least one of the vertebrae. Preferably, the surgical robot can be accommodated at any of a plurality of predefined positions along the cross member, such that the robot can perform surgical procedures on a plurality of the vertebrae. In such a case, the robot can preferably perform these surgical procedures on a plurality of the vertebrae with a single registration process. Alternatively and preferably, a surgical robot may be attached to one of the vertebrae, such that the robot can perform surgical procedures on at least one of the vertebrae. These surgical procedures can preferably be performed on a plurality of the vertebrae with a single registration process.

According to still another preferred embodiment of the present invention, the bridge can be provided with a navigational position probe associated with a computer assisted surgery system, such that the position of the bridge and of the vertebrae are known to the system.

There is further provided in accordance with yet another preferred embodiment of the present invention, a bridge assembly for use in surgery on the spine of a subject, the bridge assembly comprising (i) at least a first spinal bridge section comprising at least two support members, each of the support members being attached to one vertebra of the spine, and a cross member connecting the support members and attached thereto at positions remote from the vertebra attachment ends of the support members, and (ii) at least a second spinal bridge section having two ends, one of the ends being attached to the at least a first spinal bridge section, and a second of the ends being attached by support members to either the pelvic bone structure of the subject or the skull of the subject, wherein the support members are such that the bridge assembly is positioned proximate the vertebrae of the spine. In accordance with still another preferred embodiment of the present invention, in such a bridge assembly, the at least a second spinal bridge section may comprise two spinal bridge sections, one attached at its second end to the pelvic bone structure of the subject and the other attached at its second end to the skull of the subject, such that the bridge assembly is positioned proximate vertebrae along the entire length of the spine. In such a case, the bridge comprises a lumbar section, a cervical section and at least one thoracic bridge section. In any of the above mentioned embodiments of the present invention, the bridge assembly is preferably such that it is free to move with movement of the spine of the subject.

In accordance with still another preferred embodiment of the present invention, in the above-described bridge assembly, the bridge sections may preferably be adapted to accommodate a surgical robot such that the robot can perform surgical procedures on at least one of the vertebrae. Preferably, the surgical robot can be accommodated at any of a plurality of predefined positions along the bridge sections of the bridge assembly, such that the robot can perform the surgical procedures on a plurality of the vertebrae. In such a case, the robot can preferably perform these surgical procedures on a plurality of the vertebrae with a single registration process. Alternatively and preferably, a surgical robot may be attached to one of the vertebrae, such that the robot can perform surgical procedures on at least one of the vertebrae. These surgical procedures can preferably be performed on a plurality of the vertebrae with a single registration process.

According to still another preferred embodiment of the present invention, the bridge assembly can be provided with a navigational position probe associated with a computer assisted surgery system, such that the position of any part of the bridge assembly and of the vertebrae are known to the system.

The disclosures of the publications mentioned in this section and in other sections of the specification, are hereby incorporated by reference, each in its entirety.

BRIEF DESCRIPTION OF THE DRAWINGS

The present invention will be understood and appreciated more fully from the following detailed description, taken in conjunction with the drawings in which:

FIGS. 6 and 7 schematically show preferred embodiments of the whole spine bridge assembly described in the embodiments of FIGS. 4 and 5, but with a miniature surgical robot attached thereto; FIG. 6 shows the robot mounted on the thoracic section of the bridge, while

DETAILED DESCRIPTION OF PREFERRED EMBODIMENTS

Figure 1:
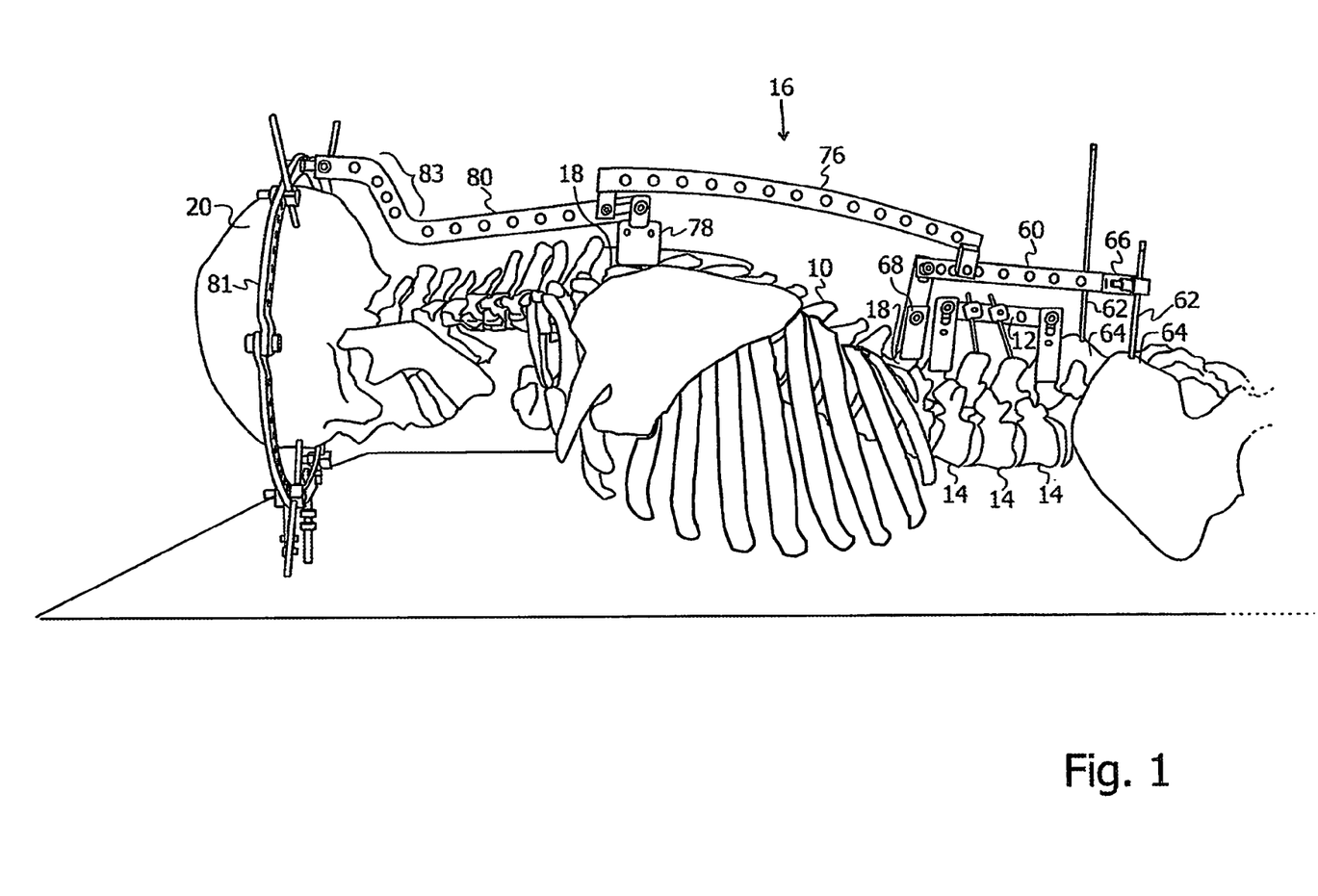
FIG. 1 is a schematic illustration of the whole of a subject's spine, showing two reference bridges, constructed and operative according to various preferred embodiments of the present invention, namely, a full-spine bridge assembly covering the whole length of the spine, and a short bridge covering several vertebrae of the lumbar section of the spine.

Reference is now made to FIG. 1, which is a schematic illustration of a model of the whole of a subject's spine, showing two reference bridges, constructed and operative according to various preferred embodiments of the present invention, for facilitating the performance of surgical procedures on the spine 10 of the subject. The illustration shows a first reference bridge 12 connecting a number of lumbar vertebrae 14 for enabling treatment of several vertebrae in a single procedure, as mentioned in application (i) hereinabove, and a second reference bridge assembly 16, composed of several bridge sections, preferably connected to a number of vertebrae 18 along the entire length of the spine, as well as to the skull 20 and the pelvis 22, as mentioned in application (ii) hereinabove. It is to be understood that the two bridges shown can generally be used either as one connected system with no mutual relative motion, or separately and independently. Each of these embodiments is now described in more detail in the drawings to follow.

Figure 2:
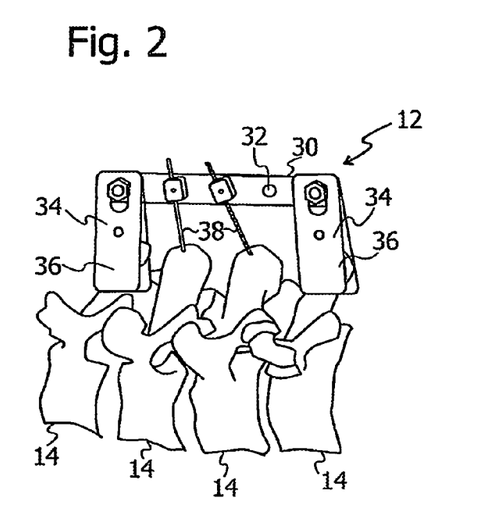
FIG. 2 illustrates schematically a close-up view of a lumbar section of a subject's spine, showing the short bridge of FIG. 1 connecting a number of lumbar vertebrae together.

Reference is now made to FIG. 2, which illustrates schematically a view of a lumbar section of a subject's spine, showing a bridge, constructed and operative according to a first preferred embodiment of the present invention, connecting a number of lumbar vertebrae together. Though this embodiment is illustrated in connection with the lumbar vertebrae, it is to be understood that it is applicable to groups of vertebrae at any level of the back. In the preferred embodiment illustrated, the bridge 12, comprising a cross member 30 with referencing holes 32, and two vertical support arms 34, is connected to the spinous processes of four adjacent vertebrae 14. When applied to a real subject, the attachment is preferably performed minimally invasively, through small incisions in the subject's skin and back tissue (not shown in any of the drawings). Though the cross members 30 are shown as simple flat elements in most of the illustrated embodiments of the present application, it is to be understand that they could also be of any other preferred form, such as rails, or angled profiles, or even a double strips, and the term cross member as claimed in the present application, is thuswise to be understood. Two preferred methods of attachment are shown in FIG. 2, the support arms 34 being preferably attached by means of clamps 36 onto the spinous processes of the outer pair of vertebrae, while the inner vertebrae are preferably connected to the cross member 30 by means of 1.5-2 mm K-wires 38 attached to their corresponding spinous processes.

Once the bridge has been mounted onto the vertebrae to be treated, the cross member 30 constitutes a platform disposed close to and above the spine, and which has a fixed position relative to each of the vertebrae connected thereto, and moves in absolute space together with the vertebrae. As described hereinabove, a preliminary registration procedure, as known in the art, can be performed to define the relative position and orientation of each of the vertebra relative to the frame itself, by means of dynamic referencing sensors, or a passive measuring arm operating as a mechanical digitizer. Once this has been done, the position of each of the vertebrae is known relative to the bridge, and if suitable pre-registration fiducials have been used, the position also of the bridge itself relative to the operation planning environment, whether a preoperative CT or MRI image, or an intra-operative X-ray fluoroscopic image, or any other image. According to one preferred method of use of the bridge of this embodiment, a miniature surgical robot, such as that described in allowed U.S. patent application Ser. No. 09/912,687, to one of the inventors of the present application, and herein incorporated by reference in its entirety, may be attached to one or more of the referencing holes 32. Such a miniature robot is then able to utilize the registration information to perform accurately positioned procedures, such as screw hole drilling, on each of the vertebrae in succession, regardless of whether the subject moves between the procedures on the successive vertebrae. This thus enables such procedures to be performed more conveniently and comfortably than by means of prior art methods, where either each vertebra is registered and operated on independently, or alternatively, if they are connected preoperatively, the subject is fixed relative to the operating table to render the connected vertebrae immobile.

According to another preferred procedure, the operation may be performed by a surgeon using hand-held tools, and an external tracking system used to relate the position of these tools to the position of the bridge and each of the vertebrae, and to the operation environment, whether predetermined by preliminary imaging, or determined intra-operatively.

Figure 3:
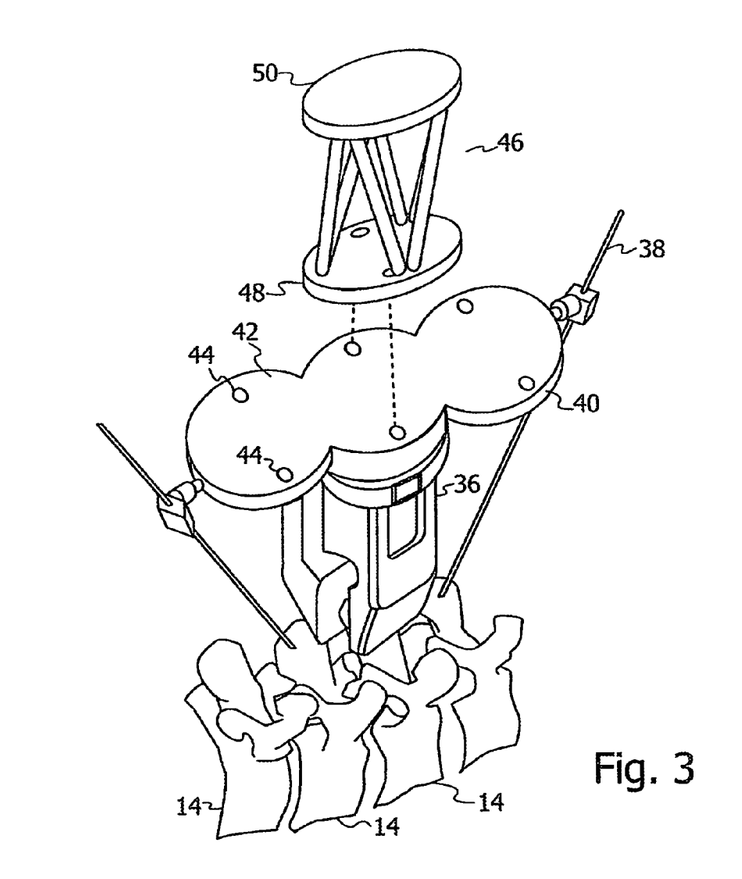
FIG. 3 is a schematic illustration of a lumbar section of subject's spine, showing a bridge, similar in function to that of the embodiment of FIG. 2, but constructed and operative according to another preferred embodiment of the present invention.

Reference is now made to FIG. 3, which is a schematic illustration of a lumbar section of subject's spine, showing a bridge, similar in function to that of the embodiment of FIG. 2, but constructed and operative according to another preferred embodiment of the present invention. Features common to those of FIG. 2 are labeled with the same reference characters. The bridge shown in FIG. 3 differs from that shown in FIG. 2 in that the cross member 40 of the bridge has a series of flat surfaces 42, with mounting holes 44 which are located to match the mounting holes of the base 48 of a miniature surgical robot 46, of the type shown below in FIGS. 6 and 7. The robot is shown in FIG. 3 ready for mounting onto the center position of the bridge. Such a preferred mounting method makes it particularly simple to move the robot from position to position when needed, while maintaining the accuracy of the registration. Though the robot in FIG. 3 is shown without any operating tools attached to its working platform 50, it is to be understood that any such tools may preferably be attached thereto, such as is described in the above mentioned allowed U.S. patent application Ser. No. 09/912,687.

The bridge of FIG. 3 also shows another preferred method of attachment to the vertebrae, whereby the center of the bridge is attached by means of a clamp, and the outer ends by means of K-wires attached to the spinous processes of the pouter vertebrae.

Reference is now made back to FIG. 1, in order to describe details of the construction and operation of the whole-spine bridge, according to another preferred embodiment of the present invention. The bridge, according to this embodiment, can preferably be divided into three separate joined component sections—a lumbar section, a thoracic section and a cervical section. It is to be understood however, that this division is only one convenient manner of constructing such a bridge, and the present invention is not meant to be limited thereby. Other preferred constructions can also be envisaged, and even partial spine bridges, where not all three sections of the spine are included, such as a lower back bridge covering from the thoracic section down to the pelvis, or an upper back bridge, covering from the thoracic section up to the skull.

The thoracic section 76 of the bridge is connected at its lower end to the lumbar section 60, and at its upper end by means of one or more clamps 78 to the spinous processes of one or more chosen vertebrae from the thoracic spine region. Alternatively and preferably, though not shown specifically in FIG. 1, one or more 1.5-2 mm K-wires are drilled into one or more chosen vertebrae from the thoracic spine region, in the same manner as K-wires are shown in FIG. 2 for use with the lumbar vertebrae. As will be described in more detail below, a sliding carriage is preferably attached to the bridge, and can be moved to any desired position along the thoracic section of the bridge, and rigidly locked preferably by means of a thumbscrew above the region of interest. A robotic system or a dynamic referencing probe can be attached to the sliding carriage, and positioned at any of several defined locations down the thoracic spine, in order to reach any desired point along the thoracic spinal region. The miniature surgical robot can preferably be mounted on the platform of the carriage, in a manner similar to that shown in FIGS. 6 and 7 hereinbelow.

At the top end of the spine, the cervical section of the bridge 80 is shown. A halo ring 81 or another commonly used fixing device, is rigidly attached on the subject's skull 20. It is to be understood that this aspect of the invention is applicable whether the fixing device is attached directly to the skull bones, such as by screws penetrating into the bone structure, or whether the fixing device is attached to the skull by means of a clamping mechanism which holds the fixing device rigidly relative to the skull by applying pressure to the skull through the skin, but without penetrating the skin. In this application, both of these types of devices are described and claimed as being "attached" on the subject's skull. The upper end of the cervical section 80 of the bridge is preferably supported by attachment to the halo ring 81. The lower end is supported either by attachment to the upper end of the thoracic section 76 of the bridge, or by means of a clamp or one or more K-wires to spinous processes suitably located near the lower cervical region. As with the lumbar 60 and thoracic bridge 76 sections, a sliding carriage is preferably attached to the bridge, and can be moved to any desired position along the thoracic section of the bridge, and rigidly locked above the region of interest. A robotic system or a dynamic referencing probe can be attached to the sliding carriage, and can thus be positioned at any of several defined locations in order to reach any desired point in the cervical spinal region. The miniature surgical robot can preferably be mounted on the platform of the carriage, in a manner similar to that shown in FIGS. 6 and 7 hereinbelow.

The cervical section of the bridge is preferably profiled to have the same approximate shape 83 as the cervical lordosis, such that the operating point of the robot mounted on the carriage remains close to the point of operation on the subject's spine.

Although in the preferred embodiment of the spinal bridge shown in FIG. 1, the thoracic section 76 of the bridge is shown anchored to the ends of the cervical 80 and lumbar 60 sections, it is to be understood that the invention is not meant to be limited thereby, but that any suitable connection scheme may be used, whereby the ends of each section of the bridge are firmly connected to their neighboring section's ends, where applicable, such that all of the sections of the bridge form one rigid structure generally parallel to the line of the spine, and are also firmly disposed relative to the vertebrae of the spine. Thus, for example, according to another preferred embodiment of the present invention, either or both ends of the thoracic section could preferably be connected directly to vertebrae, and the cervical and lumbar sections attached to the thoracic section. Furthermore, although the invention has been described using three sections of the whole-spine bridge, it is to be understood that the invention is not meant to be limited thereby, but that embodiments using two adjacent sections of the three described are also understood to be included as preferred embodiments of the present invention.

Whole spine bridges have been used previously for Halofemoral longitudinal and pelvic traction for the correction of spinal deformity. The spinal bridges of the present invention differ in that they are adapted for use in surgical procedures performed on the spine, generally to correct spinal deformities, such as scoliotic deformity. Use of the spinal bridge of the present invention improves the anatomical relationships between vertebrae on which procedures are being performed, such as by improving the accuracy with which screw insertion is made into the pedicles for attaching inserts for correcting such deformities. Additionally, the present invention may also be advantageous for providing increased accuracy in robotic screw insertion through reduction of mutual movement of adjacent vertebrae, since such mutual movement may result in degraded screw insertion accuracy. Furthermore, the use of the whole spine bridge of the present invention improves the accuracy of many surgical procedures performed using it, whether drilling, sawing, milling or even simple guidance of a surgical tool relative to the vertebrae of the whole spine, whether applied robotically or manually by the surgeon, such that the procedure is accurately performed relative to all of the vertebrae to be operated on.

Figure 4:
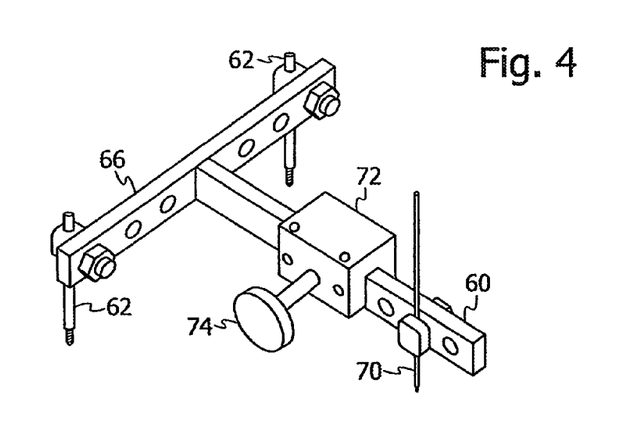
FIG. 4 is a schematic illustration of a lumbar section bridge, showing the component parts for anchoring the lumbar section to the subject's pelvis.
Figure 5:
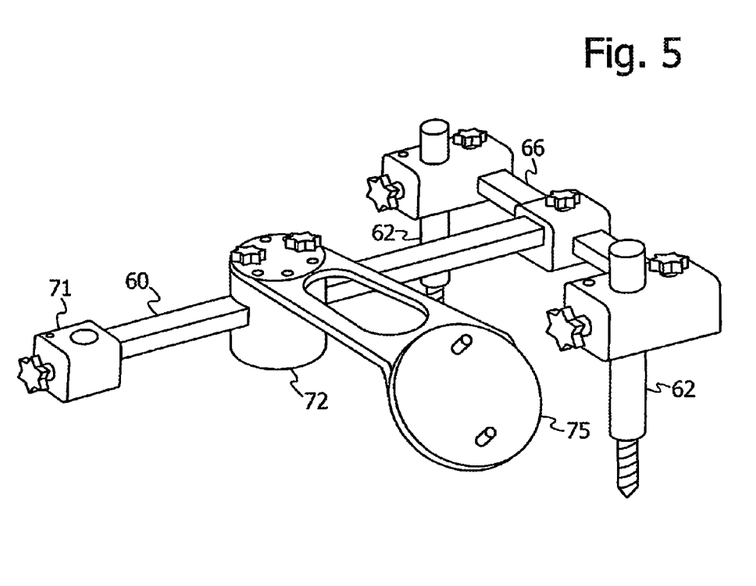
FIG. 5 is an alternative preferred embodiment of a lumbar section bridge, similar to that shown in FIG. 4.

Reference is now also made to FIGS. 4 and 5, which show further details of the lower end of the whole spine bridge, and which are to be viewed together with the details shown in FIG. 1. FIG. 4 is a schematic illustration of the lumbar section of the bridge, showing the component parts for anchoring this section to the subject's pelvis. FIG. 5 is a schematic illustration of an alternative embodiment to that shown in FIG. 4, of the lumbar section of the bridge. The lumbar bridge section 60 preferably comprises two nails 62 with screwed ends, inserted into the spina iliaca posterior superior on both right and left sides of the subject. A bar 66 is preferably attached to both screwed nails 62, in order to generate a rigid connection between the two nails, to serve as a base anchor for the lumbar section 60 of the spinal bridge. The upper end of the lumbar section of the bridge is preferably attached to a spinous process of one of the upper lumbar vertebrae, either by means of a clamp 68 as shown in FIG. 1, or by means of a K-wire 70, shown in FIG. 4, drilled into such a suitably located spinous process in the lumbar spine region. The lumbar bridge section and its component parts are preferably attached to each other by means of adjustable fittings, such that the disposition of the bridge relative to the spine can be performed with maximum flexibility to suit individual subjects.

Attached to the bridge is a sliding carriage 72, that can be moved to any desired position along the lumbar section of the bridge, and rigidly locked by means of a thumbscrew 74 above the lumbar spine region of interest. A robotic system or a dynamic referencing probe can be attached to the sliding carriage, and thus positioned at several defined orientations in order to reach any desired location along the lumbar spine. The miniature surgical robot or a dynamic referencing sensor can preferably be mounted on the platform of the carriage, in a manner similar to that shown in FIGS. 6 and 7 hereinbelow.

Reference is now made to FIG. 5, which schematically illustrates an alternative and preferable arrangement for the construction of the lumbar section of the bridge, and for anchoring this section to the subject's pelvis. Parts having the same function as those shown in the embodiment of FIG. 4, are labeled with the same reference characters, even though the structural form may be different. The sliding carriage 72 differs from that in FIG. 4 in that it has an offset table 75 on which a miniature robot is preferably mounted, such an offset table providing better lateral access to the vertebrae, such as is advantageous in the performance of translaminar or transfacet fusion procedures. Additionally, the bridge length adjustment is performed at the pelvic end and not at the upper end. The mounting block 71 at the top end can be adapted to be fixed to the spine either by means of a K-wire, as shown in FIG. 4, or by means of a spinal process clamp, as shown in FIG. 1.

Figure 6:
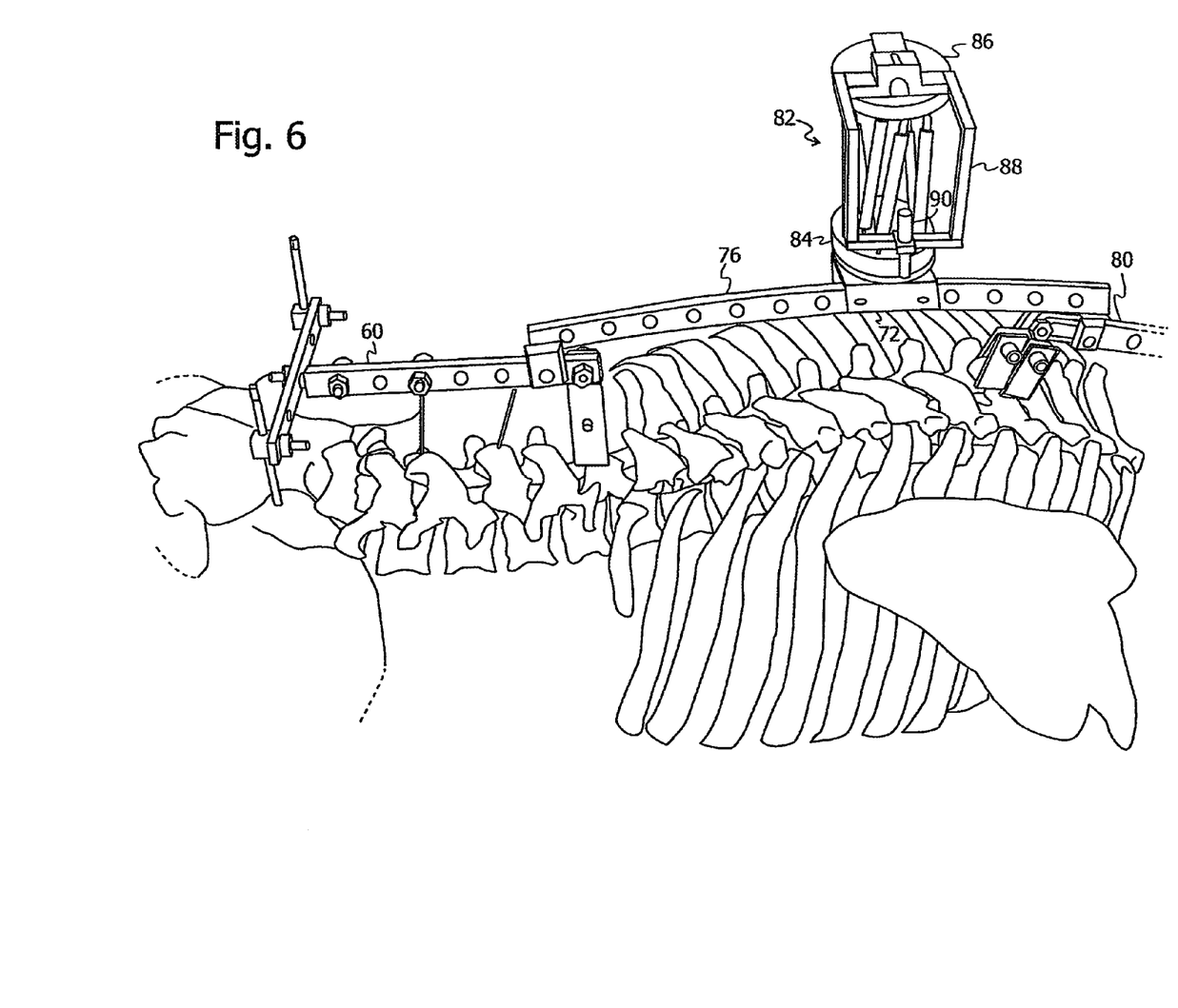
Figure 7:
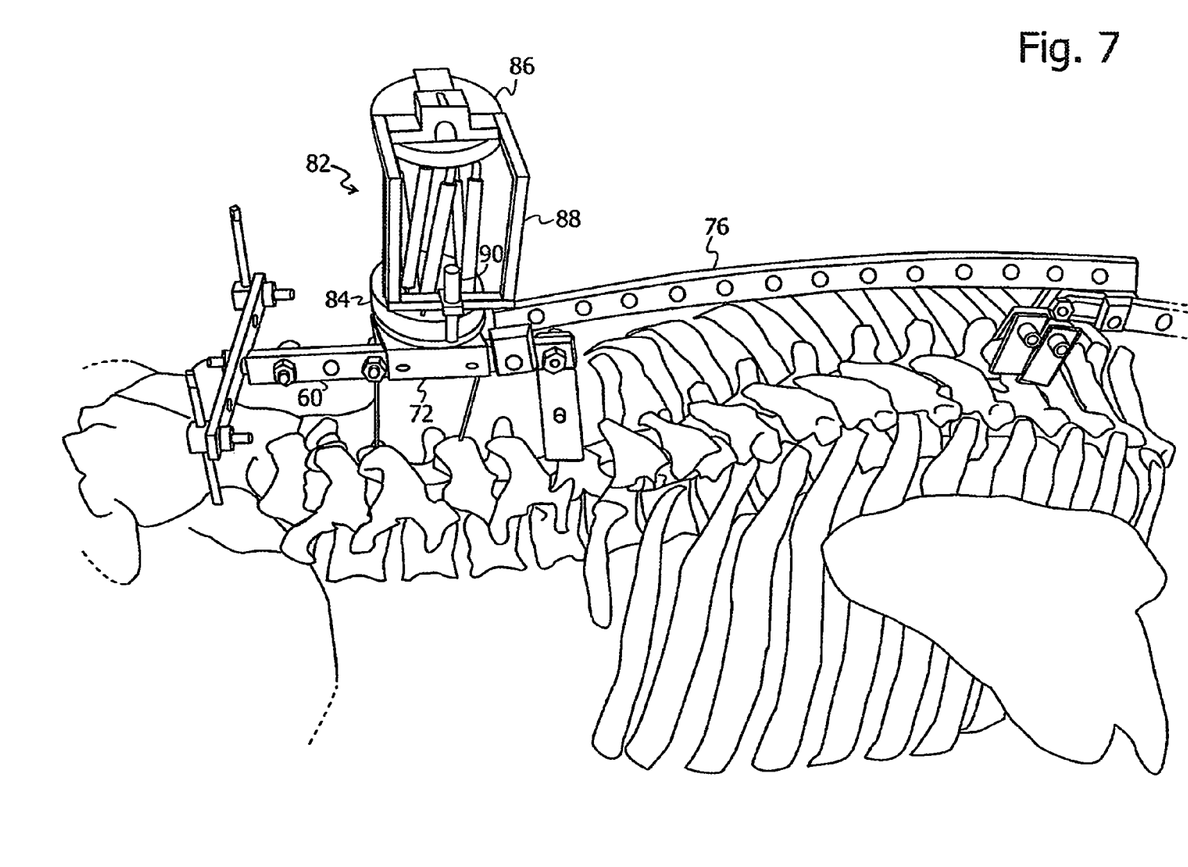
FIG. 7 shows the robot mounted on the lumbar section of the bridge.

Reference is now made to FIGS. 6 and 7, which schematically show preferred embodiments of the whole spine bridge described in the embodiment of FIG. 1, also showing attached thereto, a miniature surgical robot 82 of the type described in allowed U.S. patent application Ser. No. 09/912,687.

In FIG. 6, the robot 82 is shown attached by its base 84 to the adjustable platform 72 on the thoracic section 76 of the bridge. The top plate 86 of the preferred miniature robot shown is the surface whose motion is controlled by the robot actuators. To that surface is preferably attached a tool frame 88, which in the embodiment shown, carries a drill guide 90 for positioning the surgeon's drill accurately where required by the operation procedure. In FIG. 7, according to another preferred embodiment of the present invention, the robot 82 is shown attached by its base 84 to the adjustable platform 72 on the lumbar section 76 of the bridge. The top plate 86 of the robot shown is the surface whose motion is controlled by the robot actuators, and to that surface is preferably attached a tool frame 88, which in the embodiment shown, carries a drill guide 90 for positioning the surgeon's drill accurately when so required in the operation procedure.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method of performing surgery on the vertebrae of the spine of a subject, said method comprising:
    providing a spinal bridge,
    attaching said spinal bridge at least one end to a first vertebrae in the spine of the subject, said spinal bridge being free to follow movement of the spine of the subject;
    mounting a surgical robot on said bridge; and
    performing a surgical procedure on at least said first vertebra,
    said method being such that movement of the spine does not affect the position of said robot relative to said at least first vertebra, enabling the performance of said surgical procedure.

2. A method according to claim 1, further comprising the steps of accommodating said surgical robot at a number of predetermined locations adapted for positioning said robot on said bridge, and performing said surgery with said robot on a plurality of said vertebrae in a single procedure.

3. A method according to claim 2 and wherein said robot can perform said surgical procedures on a plurality of said vertebrae with a single registration process.

4. A method according to claim 1, further comprising the steps of mounting said robot on a moveable slide on said bridge, such that adjustment of the position of said slide on said bridge enables surgery to be performed on a plurality of vertebrae in a single procedure.

5. A method according to claim 4 and wherein said robot can perform said surgical procedures on a plurality of said vertebrae with a single registration process.

6. A method according to claim 1 and wherein said bridge is also attached to any of a second vertebra of the subject's spine, the subject's skull and the subject's pelvic bone.

7. A method according to claim 1 and wherein said step of attaching said spinal bridge to a first vertebrae is performed by means of either of a bone clamp and at least one K-wire.

8. A method according to claim 1, further comprising utilizing a navigational position probe associated with a computer assisted surgery system, such that the position of said bridge and of said first vertebra are known to said system.

* * * * *

UNITED STATES PATENT AND TRADEMARK OFFICE
CERTIFICATE OF CORRECTION

PATENT NO. : 7,887,567 B2  
APPLICATION NO. : 10/595305  
DATED : February 15, 2011  
INVENTOR(S) : Moshe Shoham et al.

Page 1 of 1

It is certified that error appears in the above-identified patent and that said Letters Patent is hereby corrected as shown below:

On the Title Page (73) Assignee: -- delete "Mazer Surgical Technologies, Ltd.," and insert -- Mazor Surgical Technologies, Ltd. --

Signed and Sealed this  
Fifth Day of April, 2011

David J. Kappos  
*Director of the United States Patent and Trademark Office*